US012806195B2

(12) United States Patent
Zhong et al.

(10) Patent No.: US 12,806,195 B2
(45) Date of Patent: Nov. 24, 2026

(54) PHARMACEUTICAL COMPOSITION AND APPLICATION THEREOF

(71) Applicant: SHANGHAI RAISING PHARMACEUTICAL CO., LTD., Shanghai (CN)

(72) Inventors: Chunjiu Zhong, Shanghai (CN); Huan Zhang, Shanghai (CN)

(73) Assignee: SHANGHAI RAISING PHARMACEUTICAL CO., LTD., Shanghai (CN)

( * ) Notice: Subject to any disclaimer, the term of this patent is extended or adjusted under 35 U.S.C. 154(b) by 832 days.

(21) Appl. No.: 18/015,096

(22) PCT Filed: Sep. 9, 2021

(86) PCT No.: PCT/CN2021/117404

§ 371 (c)(1), (2) Date: Jan. 9, 2023

(87) PCT Pub. No.: WO2022/007982

PCT Pub. Date: Jan. 13, 2022

(65) Prior Publication Data

US 2023/0248726 A1 Aug. 10, 2023

(30) Foreign Application Priority Data

Jul. 10, 2020 (CN) ......................... 202010662333.6

(51) Int. Cl.
*A61K 31/51* (2006.01)
*A61K 31/445* (2006.01)
*A61P 25/28* (2006.01)

(52) U.S. Cl.
CPC ............ *A61K 31/51* (2013.01); *A61K 31/445* (2013.01); *A61P 25/28* (2018.01)

(58) Field of Classification Search
CPC .............................. A61K 31/51; A61K 31/675
See application file for complete search history.

(56) References Cited

U.S. PATENT DOCUMENTS

2015/0209306 A1 7/2015 Bredesen et al.

FOREIGN PATENT DOCUMENTS

| | | |
|---|---|---|
| CN | 101134048 | 3/2008 |
| CN | 101317849 | 12/2008 |
| CN | 103724374 | 4/2014 |
| CN | 108904739 | 11/2018 |
| JP | 2010540668 | 12/2010 |
| JP | 2015078129 | 4/2015 |
| WO | 2006107019 | 10/2006 |

OTHER PUBLICATIONS

Shanghai Rixin Biotechnology Co., "Drug Clinical Trial Registration and Information: CTR20171631", Jan. 4, 2018. URL: http://www.chinadrugtrials.org.cn/clinicaltrials.searchlistdetail.dhtml?id=68ea55e7444c4c12a32ec6baa2e7ebc1.*

Pan, "Powerful beneficial effects of benfotiamine on cognitive impairment and b-amyloid deposition in amyloid precursor protein/presenilin-1 transgenic mice", Brain 2010: 133; 1342-1351.*

Yan Zhaofeng et al., "Anti-Alzheimer's Activity and Pharmacokinetics of Benfotiamine", World Clinical Drugs, vol. 32, No. 8, Dec. 2011 (4 pages).

Feng Xiaoling, "Causes of Alzheimer's Disease and Current Pharmacological Treatments", Medical Theory and Practice, vol. 29, Issue 4, Feb. 2016 (4 pages).

Pan X, Chen Z, Fei G, Pan S, Bao W, Ren S, Guan Y, Zhong C. Long-term cognitive improvement after benfotiamine administration in patients with Alzheimer's disease. Neuroscience bulletin. Dec. 2016;32(6):591-6.

* cited by examiner

*Primary Examiner* — Sahar Javanmard
(74) *Attorney, Agent, or Firm* — Robin L. Teskin; Baker, Donelson, Bearman, Caldwell & Berkowitz PC

(57) ABSTRACT

A pharmaceutical composition containing benfotiamine or a pharmaceutically acceptable salt thereof; and donepezil or a pharmaceutically acceptable salt thereof. Experimental results have shown that when combined administration of benfotiamine and donepezil hydrochloride, a better synergistic effect is achieved, the spatial learning memory capacity of an AD mouse can be improved relatively well, and the effect is significantly better than the effect of benfotiamine or donepezil hydrochloride when administered alone, showing that the pharmaceutical composition of the present invention has better pharmaceutical activity in the treatment of Alzheimer's disease.

13 Claims, 2 Drawing Sheets

PHARMACEUTICAL COMPOSITION AND APPLICATION THEREOF

CROSS-REFERENCE TO RELATED APPLICATIONS

This application is a U.S. National Phase application of Int'l Appl. No. PCT/CN2021/117404, filed Sep. 9, 2021, which claims priority to Chinese Appl. No. 202010662333.6, filed Jul. 10, 2020, each of which are incorporated herein by reference in their entireties.

FIELD OF THE INVENTION

The present invention belongs to the field of medicine, and particularly relates to a pharmaceutical composition comprising benfotiamine or a pharmaceutically acceptable salt thereof and donepezil or a pharmaceutically acceptable salt thereof, and to use of the pharmaceutical composition in the manufacture of a medicament for the prophylaxis or the treatment of Alzheimer's disease.

BACKGROUND OF THE INVENTION

Alzheimer's disease (AD, commonly referred to as senile dementia) is a progressive neurodegenerative disease with cognitive and behavioral disorders as the main clinical manifestations, and is also the most common type of senile dementia, mainly manifested as cognitive impairment and rapid decline in memory function. According to the World Alzheimer Report 2015, the number of global AD patients will increase to 130 million by 2050.

Donepezil (molecular formula: $C_{24}H_{29}NO_3$, donepezil hydrochloride is the common form used as medicine), is the main drug for treating AD in clinic. It can delay the progression of the middle and early stages of AD and improve the clinical symptoms of early AD by inhibiting cholinesterase and increasing the acetylcholine level.

Benfotiamine (molecular formula: $C_{19}H_{23}N_4O_6PS$; chemical name: S-2-[[(2-methyl-4-amino-5-pyrimidinyl) methyl]formylamino]-5-phosphonooxy-2,3-pentenyl-3-mercaptobenzoate, benzoylthiamineomonophosphate; abbreviation: BTMP) can improve the low bioavailability of water-soluble vitamin B1, increase the concentration of vitamin B1 in blood and tissues, thereby improving the therapeutic effect. Recent studies shows that benfotiamine can be used for the prophylaxis and the treatment of Alzheimer's disease. For example, patent CN200710041571.X discloses a pharmaceutical composition comprising benfotiamine for the treatment of Alzheimer's disease.

Although the prior art discloses the above drugs for treating Alzheimer's disease, drugs for effectively reversing or preventing the progression of the disease are not available to date. Therefore, there is a lack of drugs that are more effective and can improve patient compliance.

SUMMARY OF THE INVENTION

The technical problem to be solved by the present invention is the issue of low pharmacodynamic activity and inconvenient administration of benfotiamine or donepezil when administered alone.

To solve the above technical problem, the present invention provides a pharmaceutical composition comprising:

benfotiamine or a pharmaceutically acceptable salt thereof; and donepezil or a pharmaceutically acceptable salt thereof.

Optionally, the weight ratio of benfotiamine or a pharmaceutically acceptable salt thereof to donepezil or a pharmaceutically acceptable salt thereof is (180 to 400):(3 to 6), or (180 to 400):3, or (200 to 400):3, or 180:3, or 200:3, or 400:3.

Optionally, the pharmaceutical composition further comprises at least one pharmaceutically acceptable carrier or excipient.

Optionally, the pharmaceutically acceptable salt is hydrochloride, or hydrobromide, or sulfate, or acetate, or maleate, or tartrate.

Optionally, the pharmaceutical composition is an oral formulation, and the oral formulation is any one of tablets, capsules, granules, powder, and pills.

Optionally, the pharmaceutical composition comprises: benfotiamine and donepezil hydrochloride.

Optionally, the weight ratio of benfotiamine to donepezil hydrochloride is (180 to 400):(3 to 6).

Optionally, the weight ratio of benfotiamine to donepezil hydrochloride is 180:6, or 240:6, or 360:6, or 240:3, or 360:3.

Optionally, the weight ratio of benfotiamine to donepezil hydrochloride is (180 to 360):(3 to 6).

Optionally, the weight ratio of benfotiamine to donepezil hydrochloride is (200 to 400):(3 to 6).

Optionally, the weight ratio of benfotiamine to donepezil hydrochloride is (200 to 400):3.

Optionally, the weight ratio of benfotiamine to donepezil hydrochloride is 200:3, or 400:3.

Optionally, the pharmaceutical composition comprises 3 mg to 10 mg of donepezil hydrochloride.

Optionally, the pharmaceutical composition comprises 150 mg to 600 mg of benfotiamine.

The present invention further provides use of the pharmaceutical composition as described above in the manufacture of a medicament for the prophylaxis or the treatment of Alzheimer's disease.

Compared with the prior art, the present invention has the following advantages:

the pharmaceutical composition provided by the present invention comprises benfotiamine or a pharmaceutically acceptable salt thereof and donepezil or a pharmaceutically acceptable salt thereof. The water maze test results show that after the combined administration of benfotiamine and donepezil hydrochloride, a good synergistic effect can be achieved, the spatial learning and memory ability of AD mice is improved, and the effect is significantly better than that of benfotiamine or donepezil hydrochloride when administered alone. This demonstrates that the pharmaceutical composition of the present invention has good pharmaceutical activity in the treatment of Alzheimer's disease.

Further, the present invention can facilitate the administration and improve the patient's compliance by preparing a combined formulation of benfotiamine and donepezil hydrochloride.

DETAILED DESCRIPTION OF THE INVENTION

Figure 1:
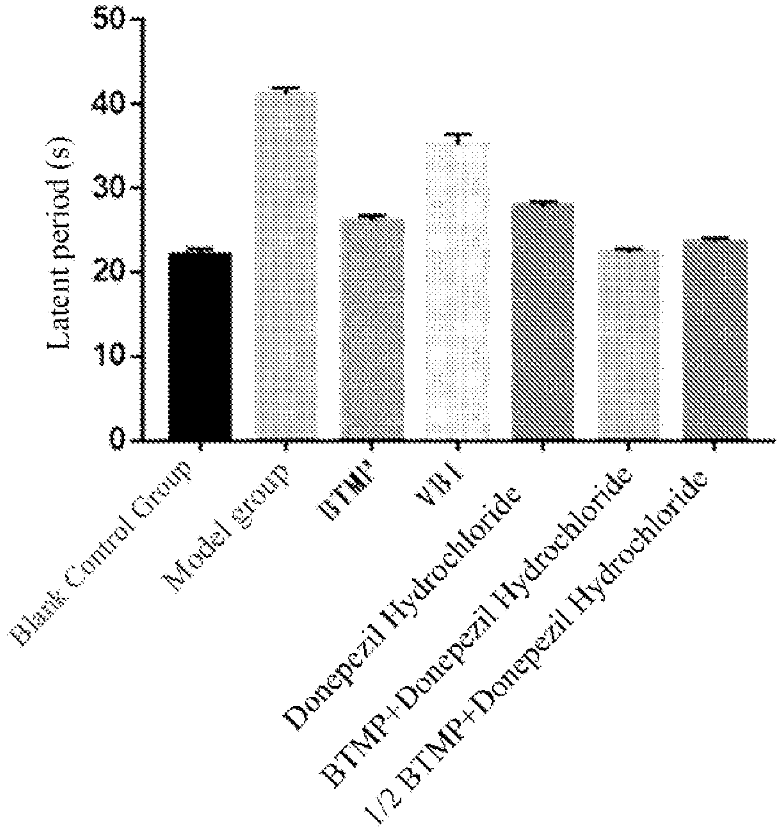
FIG. 1 shows the effect of each compound on the latent period of animals in the Example.

Although it has been disclosed in the prior art that donepezil or benfotiamine can be used alone for the treatment of Alzheimer's disease, it has not been revealed or recognized that the combination of the two drugs may be more beneficial in the manufacture of a medicament for the prophylaxis or the treatment Alzheimer's disease. The inventors find that donepezil and benfotiamine can achieve a synergistic effect which is significantly superior to that of the active ingredients when used alone.

The present invention provides a pharmaceutical composition comprising benfotiamine or a pharmaceutically acceptable salt thereof and donepezil or a pharmaceutically acceptable salt thereof. The water maze test results show that after the combined administration of benfotiamine and donepezil hydrochloride, a good synergistic effect can be achieved, the spatial learning and memory ability of AD mice is improved, and the effect is significantly better than that of benfotiamine or donepezil hydrochloride when administered alone. This demonstrates that the pharmaceutical composition of the present invention has good pharmaceutical activity in the treatment of Alzheimer's disease. Further, the present invention can facilitate the administration and improve the patient's compliance by preparing a combined formulation of benfotiamine and donepezil hydrochloride.

In order to make the foregoing objects, features and advantages of the invention to be more readily understood, a detailed description of the specific embodiments of the present invention is provided as follows.

Unless otherwise specified, the present invention is generally not particularly limited as to the source of the materials or reagents used, which, for example, may be commercially obtained.

Example 1

The effective components comprised in the composition are: benfotiamine 150 mg; and donepezil hydrochloride 5 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 2

The effective components comprised in the composition are: benfotiamine 200 mg; and donepezil hydrochloride 5 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 3

The effective components comprised in the composition are: benfotiamine 300 mg; and donepezil hydrochloride 5 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 4

The effective components comprised in the composition are: benfotiamine 400 mg; and donepezil hydrochloride 5 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 5

The effective components comprised in the composition are: benfotiamine 600 mg; and donepezil hydrochloride 5 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 6

The effective components comprised in the composition are: benfotiamine 400 mg; and donepezil hydrochloride 3 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 7

The effective components comprised in the composition are: benfotiamine 400 mg; and donepezil hydrochloride 6 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

Example 8

The effective components comprised in the composition are: benfotiamine 200 mg; and donepezil hydrochloride 6 mg.

Preparation Method:

Benfotiamine and donepezil hydrochloride APIs are weighed in the prescribed amounts, and at least one pharmaceutically acceptable carrier or excipient is added, to prepare an oral formulation. The oral formulation may be any one of tablets, capsules, granules, powder, and pills.

In the following, the effect of the pharmaceutical composition provided herein and that of benfotiamine, donepezil hydrochloride, and vitamin B1 when used alone are compared in a Morris water maze test.

Experimental Example 1: Morris Water Maze Test

1. Experimental Principle

In water, rodents have a strong motivation to escape from the water environment, and can escape from the water environment in the fastest and most direct way. The process of learning to escape from the water environment reflects the learning ability of animals. Spatial positioning according to the surrounding environment and swimming to a safe place in the water (such as a platform) on purpose can reflect the spatial learning and memory ability of animals.

2. Test Protocols 2.1. Materials (1) Test Animals

The test animals were male APP/PS1/Tau mice and C57BL/6 wild type mice. The mice were 8 months old, weighing 250-300 g, and purchased from The Jackson laboratory.

App/PS1/Tau mice are APP/PS1/tau triple transgenic Alzheimer's disease (3×Tg-AD) model mice, whose AO deposition occurs several months earlier than the pathological change of the tau protein, and can more realistically simulate the clinical process and pathological changes of Alzheimer's disease.

(2) Main Formulations

CMC-Na (sodium carboxymethyl cellulose), Shanghai Sinopharm Chemical Reagent Co., Ltd., batch No: 20181203; BTMP (benfotiamine), Shanghai Raising Biotechnology Co., Ltd., batch No: 1908002; donepezil hydrochloride, manufactured by Eisai (China) Pharmaceutical Co. Ltd., batch No: 1704019.

2.2. Drug Preparation and Administration Information (1) Drug Preparation

Preparation of 0.7% m/v CMC Na (sodium carboxymethyl cellulose): 0.7 g of sodium carboxymethyl cellulose was weighed and dissolved in 100 ml of purified water, to obtain 0.7% m/v CMC-Na.

Preparation of a 10 mg/ml vitamin B1 solution (dosage: 200 mg/kg): 500 mg of vitamin B1 was weighed, and 0.7% m/v CMC-Na was added to reach 50 ml, to obtain a 10 mg/ml solution.

Preparation of a 10 mg/ml BTMP suspension (dosage: 200 mg/kg): 500 mg of BTMP was weighed, and 0.7% m/v CMC-Na was added to reach 50 ml, to obtain a 10 mg/ml BTMP suspension.

Preparation of a 20 mg/ml BTMP suspension (dosage: 400 mg/kg): 500 mg of BTMP was weighed, and 0.7% m/v CMC-Na was added to reach 25 ml, to obtain a 20 mg/ml BTMP suspension.

Preparation of a 0.075 mg/ml donepezil hydrochloride suspension (dosage: 1.5 mg/kg): one donepezil hydrochloride tablet (containing 5 mg donepezil hydrochloride) was ground, and 0.7% m/v CMC-Na was added to reach 66.67 ml, to obtain a 0.075 mg/ml donepezil hydrochloride suspension.

Preparation of a 0.15 mg/ml donepezil hydrochloride suspension (dosage: 3.0 mg/kg): one donepezil hydrochloride tablet (containing 5 mg donepezil hydrochloride) was ground, and 0.7% m/v CMC-Na was added to reach 33.33 ml, to obtain a 0.15 mg/ml donepezil hydrochloride suspension.

Preparation of a 10 mg/ml BTMP suspension+0.075 mg/ml donepezil hydrochloride suspension (dosage: 200 mg/kg BTMP suspension+1.5 mg/kg donepezil hydrochloride suspension): a 20 mg/ml BTMP suspension and a 0.15 mg/ml donepezil hydrochloride suspension were respectively prepared, and equal volumes were evenly mixed before administration, to obtain a 10 mg/ml BTMP suspension+0.075 mg/ml donepezil hydrochloride suspension.

Preparation of a 5 mg/ml BTMP suspension+0.075 mg/ml donepezil hydrochloride suspension (dosage: 100 mg/kg BTMP suspension+1.5 mg/kg donepezil hydrochloride suspension): a 10 mg/ml BTMP suspension and a 0.15 mg/ml donepezil hydrochloride suspension were respectively prepared, and equal volumes were evenly mixed before administration, to obtain a 5 mg/ml BTMP suspension+0.075 mg/ml donepezil hydrochloride suspension.

(2) Administration Information

| Test Grouping | Drugs | Dosage/ per day | Intragastric administration specification | Number of animals | Animal genotype |
|---|---|---|---|---|---|
| Blank control group | Blank drug (0.7% m/v CMC-Na) | / | 0.2 ml/10 g body weight | 10 | C57BL/6 wild type |
| Model group | | / | 0.2 ml/10 g body weight | 10 | APP/PS1/Tau |
| Test group | Positive control drug: benfotiamine (BTMP) | 200 mg/kg | 0.2 ml/10 g body weight | 10 | APP/PS1/Tau |
| | Vitamin B1 (VB1) | 200 mg/kg | 0.2 ml/10 g body weight | 10 | APP/PS1/Tau |
| | Donepezil hydrochloride | 1.5 mg/kg | 0.2 ml/10 g body weight | 10 | APP/PS1/Tau |
| | BTMP + donepezil hydrochloride | 200 mg/kg + 1.5 mg/kg | 0.2 ml/10 g body weight | 10 | APP/PS1/Tau |
| | ½BTMP + donepezil hydrochloride | 100 mg/kg + 1.5 mg/kg | 0.2 ml/10 g body weight | 10 | APP/PS1/Tau |

2.3. Test Method

The mice in the blank control group, the model group and the test groups were intragastrically administered according to the dosage/specification in 2.2. for 8 weeks, and the water maze training and testing were started in the last week of the administration. The water maze training and testing lasted for 6 days, with 5 days of training and 1 day of testing. In addition, during the water maze training and testing period (6 days in total), conditions such as the indoor lighting etc. were kept constant, and the room was kept quiet, so as to eliminate the interference of the environment and personnel.

(1) Pre-test preparation: an appropriate amount of water was placed in a water maze pool with water temperature being kept at 22±3° C., a platform was placed at a fixed position (the target quadrant) and 1 cm below the water surface, and titanium dioxide was added until water color was white, and the platform could not be seen clearly.

(2) Training period (Day 1 to Day 5): each mouse was placed on the platform for 15 s (to increase the mouse's sense of security on the platform) prior to the first quadrant training on each day, and then the mouse was placed in the quadrant where the platform located in the pool (head towards the wall), and a swimming time of 60 s was set. If it found the platform within 60 s and stayed for 5 s, it was considered as a success in finding the platform. If it did not find the platform, the time was recorded as 60 s, and the mouse was guided to the platform to stay for 20 s, after which the mouse was taken out, and the training of this mouse in this quadrant was terminated.

After the first quadrant training, the training in the remaining three quadrants was performed in turn, wherein it is not necessary to place the mice on the platform and hold for 15 s before training. The interval between two quadrant training of each mouse was 10-15 minutes. The training was performed for 5 consecutive days in this manner.

(3) Testing period (Day 6): after 24 hours from the completion of the last training, the platform was removed, and the mouse was dropped at the site opposite to the initial platform quadrant (i.e., the position farthest from the platform). The time of the mouse in the target quadrant (the quadrant where the platform initially located), the times of crossing over the initial platform position (the times of crossing over the platform) and the time of first crossing over the initial platform position (the latent period) were recorded, which were used as the indexes for assessing the spatial learning and memory ability of the mouse.

3. Test Results

Compared with the blank control group, the latent period of the mice in the model group increased significantly, the times of crossing over the platform decreased, and the time in the target quadrant decreased significantly, with significant difference. The results demonstrate that the transgenic mice are different from the normal mice in spatial learning and memory ability, and thus are suitable for spatial learning and memory training. Compared with the model group, the positive control group and the test groups showed significant improvement in the latent period, the times of crossing over the platform and the time in the target quadrant, all with significant difference. The results are shown in Table 1.

TABLE 1

Morris water maze test results of mice in each compound group (n = 10)
Morris water maze test data analysis

| Group | latent period (s) | Times of crossing over the platform | Time in the target quadrant (s) |
|---|---|---|---|
| Blank control group | $22.10 \pm 2.18^{\#\&}$ | $2.90 \pm 0.74^{\#}$ | $17.51 \pm 2.03^{\#\&}$ |
| Model group | $41.10 \pm 2.51^{*\&}$ | $0.70 \pm 0.82^{*\&}$ | $9.93 \pm 1.41^{*\&}$ |
| BTMP | $26.10 \pm 1.85^{*\#}$ | $2.10 \pm 0.74^{\#}$ | $14.96 \pm 1.50^{*\#}$ |
| VB1 | $35.10 \pm 4.09^{*\#\&}$ | $1.00 \pm 0.67^{*\&}$ | $11.87 \pm 1.17^{*\#\&}$ |
| Donepezil hydrochloride | $27.80 \pm 2.04^{*\#}$ | $1.80 \pm 0.79^{*\#}$ | $14.44 \pm 1.11^{*\#}$ |
| BTMP + donepezil hydrochloride | $22.30 \pm 1.49^{\#\&}$ | $2.60 \pm 0.97^{\#}$ | $16.41 \pm 1.22^{\#}$ |
| ½ BTMP + donepezil hydrochloride | $23.60 \pm 1.51^{\#}$ | $2.40 \pm 0.52^{\#}$ | $15.43 \pm 0.83^{*\#}$ |

Figure 2:
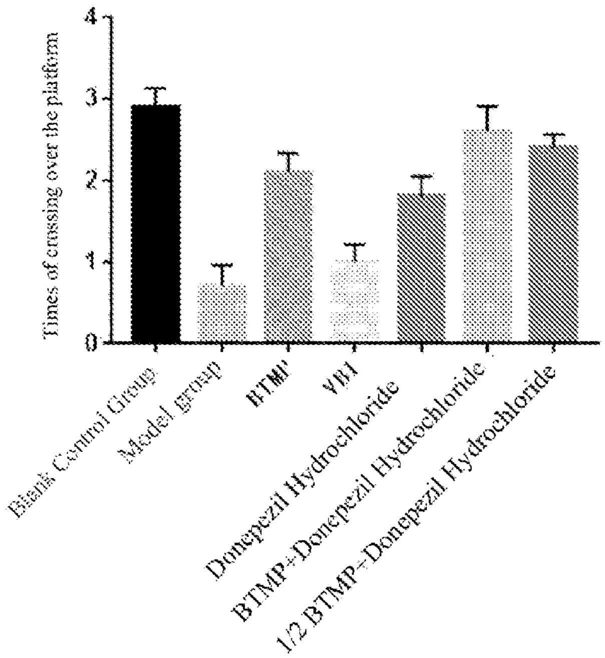
FIG. 2 shows the effect of each compound on the number of times of crossing over the platform of animals in the Example.
Figure 3:
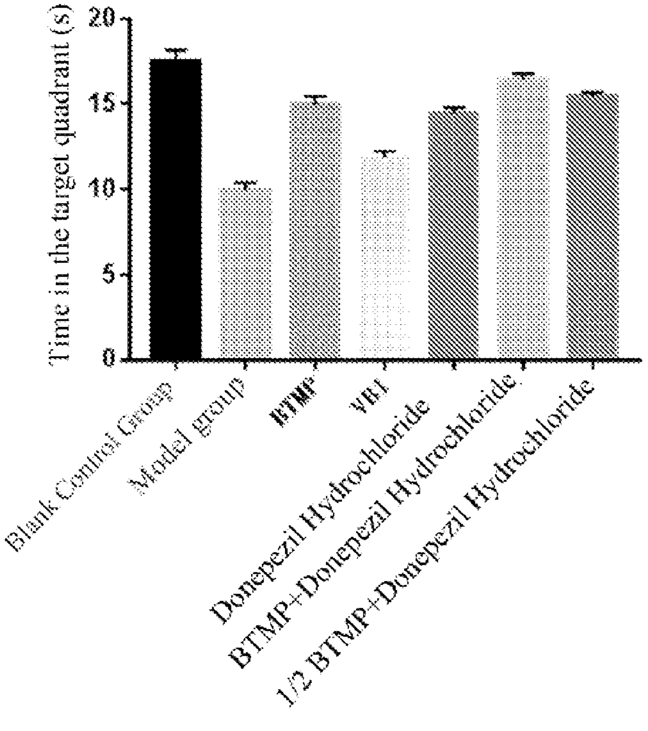
FIG. 3 shows the effect of each compound on the time spent in the target quadrant of animals in the Example.

Notes:
P < 0.05 indicates significant difference;
*P < 0.05-compared to the blank control group;
$^{\#}$P < 0.05-compared to the model group;
$^{\&}$P < 0.05-compared to BTMP Taking the latent period, the times of crossing over the platform and the time in the target quadrant as indexes for assessing the compound efficacy, the order was the blank control group, BTMP+donepezil hydrochloride, ½ BTMP+donepezil hydrochloride, BTMP, donepezil hydrochloride, VB1 and the model group (ranked in order of superior performance). The results are shown in FIG. 1 to FIG. 3. The results show that VB1 did not significantly improve the learning and memory of the AD mice, while BTMP, donepezil hydrochloride, BTMP+donepezil hydrochloride, ½ BTMP+donepezil hydrochloride significantly improved the spatial memory and learning ability of the AD mice, and the combined administration of BTMP and donepezil hydrochloride achieved the best effect in improvement, which was significantly better than that of BTMP and donepezil hydrochloride when used alone.

The water maze test results in the present invention show that after the combined administration of benfotiamine and donepezil hydrochloride, a good synergistic effect can be achieved, the spatial learning and memory ability of the AD mice is improved, and the effect is significantly better than that of benfotiamine or donepezil hydrochloride when administered alone, and also better than that of vitamin B1. The pharmaceutical composition of the present invention has good pharmaceutical activity in the treatment of Alzheimer's disease.

Experimental Example 2: Clinical Trial

A 52-week clinical trial study was conducted in patients with a moderate Alzheimer's disease (MMSE 10-19 at screening). Study grouping and administration regimen were as follows:

| Grouping | Administration regimen |
|---|---|
| Treatment group (number of participants: 64) | 300 mg of benfotiamine was orally administered at half an hour after breakfast on each day; at half an hour after dinner on each day, 300 mg of benfotiamine was orally administered and 5 mg of donepezil hydrochloride was orally administered simultaneously; and the administration was continued for 52 weeks. |
| Placebo group (number of participants: 61) | 300 mg of benfotiamine simulant was orally administered at half an hour after breakfast on each day; at half an hour after dinner on each day, 300 mg of benfotiamine simulant was orally administered and 5 mg of donepezil hydrochloride was orally administered simultaneously; and the administration was continued for 52 weeks. |

The patients were scored at 12, 24, 36, and 52 weeks after administration based on the ADAS-cog scale (including 11 items (word recall, naming, execution of command, structure exercise, intention exercise, orientation, word recognition, remembering test instructions, verbal expression ability, word finding ability, and language comprehension ability) for assess the cognitive function level of a patient, with a score range of 0-70, the higher the score is, the severer the cognitive impairment is). The intergroup differences in changes of patient scores relative to the baseline are shown in the following table.

| Difference between the treatment group and the placebo group | Lsmeans | 95% CIL | 95% CIU | p-value |
|---|---|---|---|---|
| 12-week change | −0.691 | −2.218 | 0.837 | 0.375 |
| 24-week change | −1.601 | −3.681 | 0.479 | 0.131 |
| 36-week change | −2.116 | −4.465 | 0.233 | 0.077 |
| 52-week change | −3.331 | −6.329 | −0.334 | 0.029 |

Note:
Lsmeans were derived from the MMRM model calibration baseline.

According to the above results, the ADAS-cog score of patients in the treatment group had better improvement than that in the placebo group. In particular, patients in the treatment group improved by 2.116 in the ADAS-cog score at 36 weeks with a statistical difference (p=0.077) and improved by 3.331 in the ADAS-cog score at 52 weeks with a statistical difference (p=0.029). The results demonstrate that the combination therapy of benfotiamine and donepezil hydrochloride can significantly delay the progression of Alzheimer's disease.

Meanwhile, during the administration, no significant drug-related adverse reactions were observed in the patients of the treatment group, indicating that the combination therapy of benfotiamine and donepezil hydrochloride has a good safety profile, and the patients are well tolerated to this therapy.

Although the invention is disclosed above, the invention is not limited thereto. Various changes and modifications may be made by one skilled in the art without departing from the spirit and scope of the invention, which is limited only by the scope of the appended claims.

What is claimed is:

1. A single pharmaceutical composition for oral administration, characterized in that the single pharmaceutical composition comprises:

benfotiamine or a pharmaceutically acceptable salt thereof; and donepezil or a pharmaceutically acceptable salt thereof, wherein said benfotiamine or a pharmaceutically acceptable salt thereof and said donepezil or a pharmaceutically acceptable salt thereof are both comprised in the same orally administrable dosage form;

wherein the weight ratio of benfotiamine or a pharmaceutically acceptable salt thereof to donepezil or a pharmaceutically acceptable salt thereof in the orally administrable dosage form ranges from (200 to 400:3), inclusive.

2. The pharmaceutical composition according to claim 1, characterized in that the weight ratio of benfotiamine or a pharmaceutically acceptable salt thereof to donepezil or a pharmaceutically acceptable salt thereof in the orally administrable dosage form is 200:3 or 400:3.

3. The pharmaceutical composition according to claim 1, characterized in that the orally administrable dosage form further comprises at least one pharmaceutically acceptable carrier or excipient.

4. The pharmaceutical composition according to claim 1, characterized in that the pharmaceutically acceptable salt is hydrochloride, or hydrobromide, or sulfate, or acetate, or maleate, or tartrate.

5. The pharmaceutical composition according to claim 1, characterized in that the orally administrable dosage form is selected from tablets, capsules, granules, powder, and pills.

6. The pharmaceutical composition according to claim 1, characterized in that the orally administrable dosage form comprises: benfotiamine and donepezil hydrochloride.

7. The pharmaceutical composition according to claim 6, characterized in that the weight ratio of benfotiamine to donepezil hydrochloride in the orally administrable dosage form is (200 to 400):3.

8. The pharmaceutical composition according to claim 7, characterized in that the weight ratio of benfotiamine to donepezil hydrochloride in the orally administrable dosage form is 240:3, or 360:3.

9. The pharmaceutical composition according to claim 7, characterized in that the weight ratio of benfotiamine to donepezil hydrochloride in the orally administrable dosage form is (200 to 360):3.

10. The pharmaceutical composition according to claim 9, characterized in that the weight ratio of benfotiamine to donepezil hydrochloride in the orally administrable dosage form is 200:3, or 400:3.

11. The pharmaceutical composition according to claim 1, characterized in that the orally administrable dosage form comprises 3 mg to 10 mg of donepezil hydrochloride.

12. The pharmaceutical composition according to claim 1, characterized in that the orally administrable dosage form comprises 150 mg to 600 mg of benfotiamine.

13. A method for the treatment of Alzheimer's disease, comprising administering to a subject in need thereof the pharmaceutical composition according to claim 1.

* * * * *